United States Patent [19]

LeMay

[11] 4,066,900

[45] Jan. 3, 1978

[54] TECHNIQUE FOR CAT UTILIZING COMPOSITE BEAM PATHS WHICH ARE WIDER AT THEIR ENDS THAN THEREBETWEEN

[75] Inventor: Christopher Archibald Gordon LeMay, Osterley, England

[73] Assignee: EMI Limited, Hayes, England

[21] Appl. No.: 698,047

[22] Filed: June 21, 1976

Related U.S. Application Data

[63] Continuation-in-part of Ser. No. 668,518, March 19, 1976, Pat. No. 4,031,395.

[51] Int. Cl.² .................. A61B 6/02; G01N 23/08
[52] U.S. Cl. ................... 250/360; 250/445 T
[58] Field of Search ............. 250/445 T, 360

[56] References Cited

U.S. PATENT DOCUMENTS 4,031,395  6/1977  LeMay .................. 250/445 T

Primary Examiner—Alfred E. Smith
Assistant Examiner—T. N. Grigsby
Attorney, Agent, or Firm—Cooper, Dunham, Clark, Griffin & Moran

[57] ABSTRACT

In a radiographic apparatus, a source of radiation is arranged to scan a planer spread of radiation in a plane (or substantially in a plane) about the body of a patient being examined. A plurality of detector devices is arranged to provide data representing the absorption of the radiation along a plurality of paths within the spread, for different orientations in the plane, for processing to determine a distribution of absorption coefficients for a planar (or substantially planar) slice of the body. The arrangement is such that a predetermined number of the detector devices is irradiated by the spread of radiation at any time, and the actual devices irradiated change progressively as the scan progresses.

14 Claims, 9 Drawing Figures

TECHNIQUE FOR CAT UTILIZING COMPOSITE BEAM PATHS WHICH ARE WIDER AT THEIR ENDS THAN THEREBETWEEN

REFERENCE TO RELATED APPLICATION

This is a continuation-in-part of U.S. Pat. application Ser. No. 668,518, filed on Mar. 19, 1976 in the mame of the same inventor, and now U.S. Pat. No. 4,031,395. The entire subject matter of said earlier application is hereby incorporated by reference into this specification.

BACKGROUND, SUMMARY AND DETAILED DESCRIPTION OF THE INVENTION

The invention relates to radiographic apparatus of the kind arranged to provide a representation of the variation of absorption with position across a planar (or substantially planar) slice of a body with respect to penetrating radiation.

In U.S. Pat. No. 3,946,234 there is described an apparatus for that purpose which includes a source of penetrating radiation arranged to provide a fan-shaped spread of radiation lying in the plane of the slice. Suitable collimators are provided to define a plurality of pencil beams from that spread, and an array of detectors is arranged to measure the intensity of each of those beams after passage through the body. The detectors are required to provide output signals indicative of the absorption suffered by the radiation over a large number of paths through the body. For that purpose the source and detectors are reciprocated in the plane of the slice and orbited about a common axis normal to that plane. The output signals are processed by any suitable method, for example the convolution method described in U.S. Pat. No. 3,924,129, to provide the desired representation.

Further developments of the apparatus are described in U.S. Pat. No. 3,937,963 and U.S. Pat. application Ser. No. 544,799, filed on Jan. 28, 1975. According to those specifications, the fan-shaped spread of radiation subtends an angle sufficient to include the whole region of interest in then plane of the slice so that a complete scan can be effected solely by orbiting the source and detectors about the common axis.

It is an object of the present invention to provide an alternative apparatus for the purpose of providing a similar representation of the variation of absorption with position across a planar (or substantially planar) slice of a body with respect to penetrating radiation.

According to the invention there is provided apparatus for examining a body by means of penetrating radiation including means for generating output signals, representative of the absorption suffered by the radiation in passage along respective beam paths through a region of the body, for processing to provide a representation of the distribution of absorption of the radiation in the region, and combining means for combining groups of output signals relating to groups of beam paths, chosen so that the beam paths of a group pass through a common elemental area of the region from different directions, to provide composite output signals representing the absorption of the radiation in passage through the body along composite beam paths, which are narrower in the vicinity of the respective elemental areas than in other parts of the region, so that the said processing can be effected on a plurality of output signals including at least some of said composite output signals.

In order that the invention may be clearly understood and readily carried into effect, examples thereof will now be described with reference to the accompanying drawings of which:

Figure 1A:
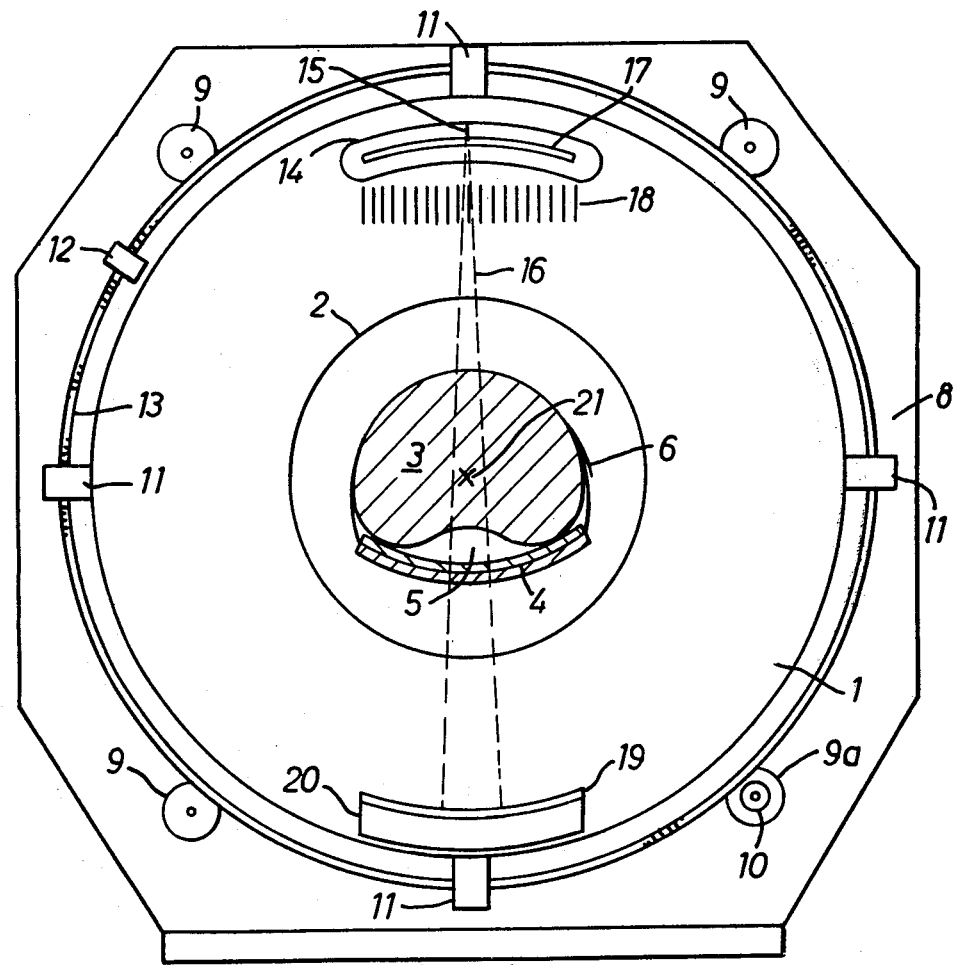
FIG. 1a and 1b show in simplified form, in end and side elevation respectively, an apparatus incorporating the invention.
Figure 1B:
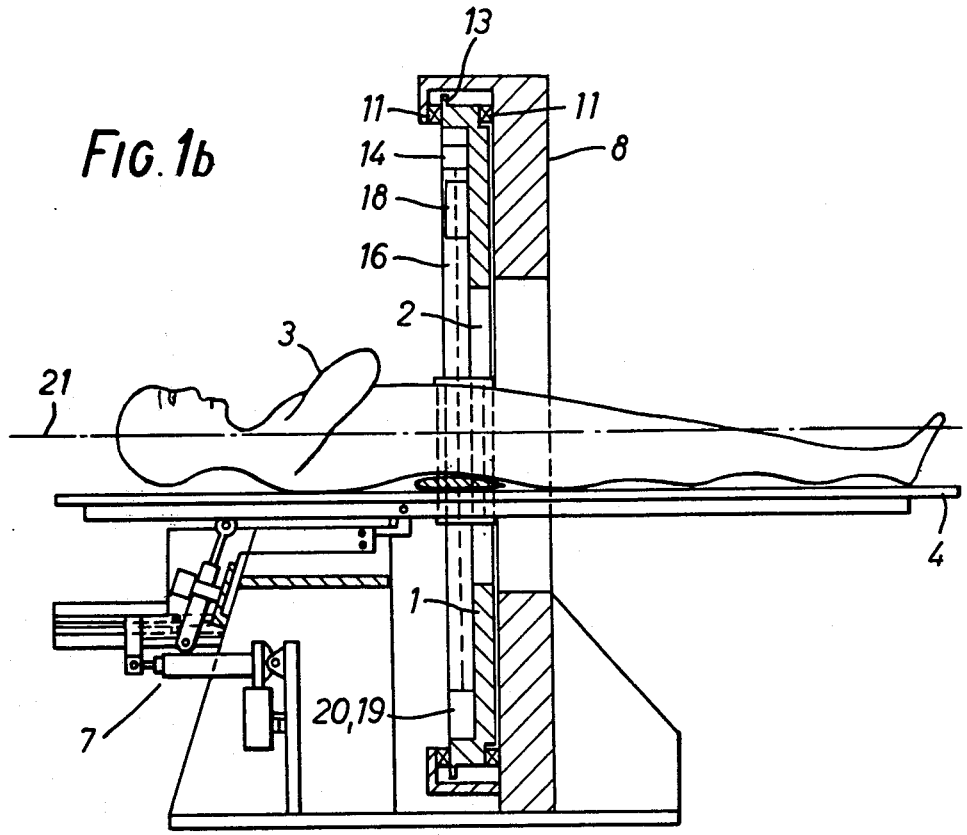

One form of the invented, apparatus is shown in a simplified form in end elevation in FIG. 1a a..d in side elevation in FIG. 1b and comprises a rotary member 1, which is rotatable about an aperture 2 in which the body 3 of a patient to be examined can be inserted. The body 3, shown in transverse section, is supported on a suitably shaped bed 4, also shown in transverse section. A material 5, having an absorption to the radiation similar to body tissue, is positioned between the body 3 and the bed 4 to substantially exclude air from the gap therebetween and is extended partly about the body to provide an approximately circular cross section to the radiation. The body is retained firmly in the desired position by means such as a restraining strap 6. If desired, a more rigid arrangement, such as that shown in U.S. Pat. No. 3,946,234, can be used. Means for properly positioning bed 4 may take any suitable form and are indicated generally at 7. The rotary member 1 is rotatably mounted on a fixed frame 8, having an aperture at least commensurate with aperture 2. Member 1 is rotated by means of a gear wheel 9a journalled in frame 8 and driven by a motor 10. The gear wheel 9a engages gear teeth, now shown, fromed around the periphery of member 1. Other, non-driven, gear wheels 9, also journalled in frame 1a, are also provided to properly support rotary member 1, and bearings 11 are provided to restrict axial motion. A light source/photocell device 12, fixed to main frame 18, cooperates with a graticule 13 to provide pulses indicative of the progress of the rotary motion. Graticule 13 is formed around the entire circumference of member 1 and comprises a transparent substrate having opaque markings formed thereon. By interrupting the light path between light source and photocell, these markings provide the desired pulses. Other means of providing suitable pulses may, of course, be used.

The rotatable member 1 carries a source 14 of penetrating radiation. This may be similar to the source described in U.S. Pat. Application Ser. No. 608,276, filed on Aug. 27, 1975, in which a substantially point source 15 of X-rays 16 is scanned over an elongated anode 17 by the scanning of an incident electron beam (by means not shown). The X-rays 16, which are confined to a fan-shaped spread by suitable collimator means 18, are, after passage through the body, incident on a detector means 19. Detector means 19 is described in greater detail hereinafter.

Also carried on member 1 is the collimator arrangement 18. This comprises, in this example, a plurality of thin parallel plate collimators, made of molybdenum or other suitable material, which are arranged to define the X-rays 16 into a narrow fan of X-rays directed at detector 19 and having the same angular spread for all positions of the spot 15. Other collimators, not shown, restrict the X-rays to the plane of the slice to be examined. The collimators are shown in simplified form in FIG. 1, and in one practical example are plates two thousands of an inch (mils) thick, 900 mils long and at 18 mils spacing. Considering a typical dimension of X-ray spot 15 on the anode 17 of the tube 14 to be 80 mils diameter, it will be apparent that the fan of X-rays is formed by four or five collimator slits so that the motion of the X-ray fan, on detector 19, in response to movement of spot 15 is substantially steady. It should be noted that the intensity distribution across the fan, produced by the collimator arrangement, should be taken into account in processing. A collimator arrangement of the dimensions given can be used to give a fan of about 2° extent if placed at a suitable distance from the source. In this example of the invention a fan of substantially 1.8° is considered.

The detector means 19 comprises a strip of individual detectors such as scintillator crystals or photodiodes, lying in the plane of the slice to be examined so as to intercept substantially all of the X-rays 16 for all positions of the spot 15. As shown in FIG. 1a, this strip of detectors is only irradiated over a small portion at any time. For the purposes of explanation it will be assumed that 3cm of the strip is so irradiated at any time. The detector comprises detector elements each covering 1mm of the strip, so that thirty such elements supply data across the 3cm of the fan. This data corresponds to thirty individual beam paths in the fan. The entire detector is typically 30cm long including 300 detector elements. In this example the detectors are scintillator crystals co-operating with photomultipliers indicated generally at 20.

In operation, the X-ray spot is scanned steadily across the anode 17 of tube 14 and correspondingly the fan of X-rays 16 scans in a plane across body 3 and surrounding materials and along detector strip 19. In this example, the irradiated region of the detectors moves in the same direction as, and approximately parallel to, the source spot 15 as a result of the form of collimators 18 used. The outputs of the detector elements are integrated for a period in which the irradiated region of the detectors is moved 1mm so that each detector provides one datum for a respective beam path. For the immediately following integration interval the data are obtained for elements displaced one place in the direction of scan i.e., with an extra element at one end of the irradiated region and one less at the other. The detector elements irradiated are thus progressively changed as the scan progresses.

It can be seen that by this means the information relating to any one small region of the body is obtained by many detectors so that the effect of relative detector errors is reduced.

To irradiate the body over a sufficient number of beam paths, source 14 and detector means 19 are in this example orbited about an axis 21 perpendicular to the slice of the body 3 to be examined. This may be achieved in steps between each scan of the spot 15. However, since the angle of the fan is 1.8°, this will be the required orbital movement for one lateral scan, and it is sufficiently small to be provided by a continuous orbital movement without significant distortion or misplacement of the beam paths.

As mentioned hereinbefore, at any time only a small proportion of the detector elements of detector means 19 are irradiated, typically 30 out of 300. That situation is utilized in the detector arrangement shown in FIG. 2. The figures shows, for the sake of clarity, a simplified arrangement for which detector means 19 comprises 25 detector elements, in the form of scintillation crystals, of which only five are irradiated at any time. The intensity of light emitted by the scintillators is measured by five photomultipliers $20_1$ to $20_5$, each of which receives light from five detector elements through individual light guides 22. The light guides are represented in the Figure by single lines. However, it will be understood that each light guide in practice receives light from one entire face of a crystal, the other faces being silvered to prevent loss of light. The light guides 22 are arranged so that the photomultipliers receive light from detector elements in interlaced manner. In this example, each receives light from elements spaced five positions apart. It will be seen from FIG. 2 that, although each photomultiplier receives light from five detector elements, only one of these will be irradiated at any time. Thus, for the position of X-ray fan 10 shown in FIG. 2, each photomultiplier receives light along the first light guide from the right, at the multiplier, and no light along the others. As the fan moves one element to the left, only the light to photomultiplier $20_5$ changes so that light is received along the second light guide. It will be apparent that, in this manner, the 25 detector elements can be covered by the 5 multipliers if the data from those multipliers is appropriately allocated in the processing used. Other numbers of detector elements and photomultipliers may be used in a similar manner.

Instead of using five different photomultipliers, a five, or more, channel photomultiplier can be used. This may be of the type described in U.S. Pat. No. 3,872,337 This may equally well be a three hundred channel photomultiplier if desired. In that case the photomultiplier can be placed close to the detector elements with short, or no, light guides so that each element would at all times supply light to one photomultiplier channel. However, since, as described above, only a small number of detector elements are irradiated at any time a grouping similar to that of FIG. 2 can be effected by joining the photomultiplier channel anodes in groups internally. By this means the number of output connections required would be reduced, simplifying construction problems. As in the previous example, other numbers of irradiated elements and groupings may be employed as desired.

Figure 2:
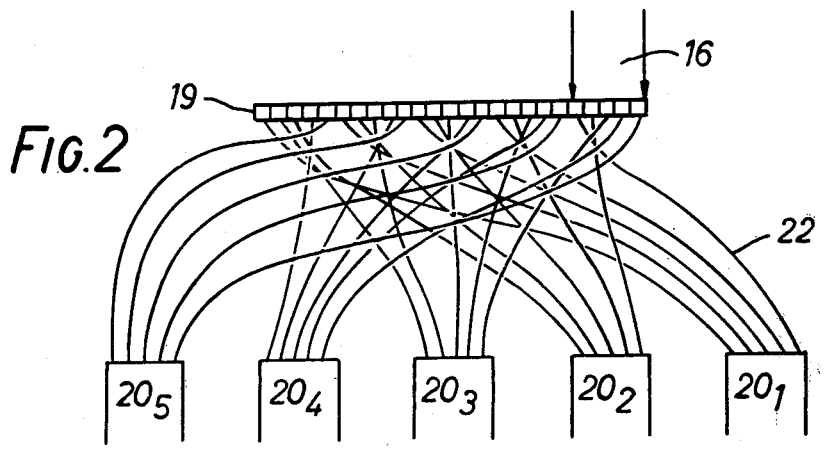
FIG. 2 shows a detector arrangement for one example of the invention.

It should be understood that FIG. 2 is illustrative of a manner of organizing the detector output. However, other positions, for example of photomultipliers 20, can be adopted for convenience of construction.

As mentioned hereinbefore, large numbers of detector elements are employed in a practical arrangement, typically 300 arranged in six cycles of 50 elements. Fifty detector elements, say 1mm apart, can be irradiated by the narrow fan of X-rays, the individual fifty beam paths being narrow enough to give the desired spatial resolution within the body. This results, however, in a large quantity of output data and, since the angular resolution so obtained is unnecessarily good, some of this data may be combined to give reduced angular resolution. The arrangement in this example is that data for beam paths passing through substantially the same parts of the body should be combined. In practice this means that data for each beam in the fan is combined with data obtained from beams incident on a number of, say three, adjacent detectors and passing through the same predetermined point in the body. A time delay of $\tau$ of seconds is applied between those adjacent detectors. The delay $\tau$ is equal to the time which elapses between the passage of a beam incident on one detector through the predetermined point and the passage of a beam incident on the next detector through the same point. The data for the first detector is delayed $\tau$ seconds and added to that of the second, and the two are delayed by a further $\tau$ seconds and added to the data for the third detector. The arrangement is assumed to be that employing continuous orbital motion; thus the three beam paths for which data is combined are not strictly parallel but give a composite beam path which is narrower at the center of the body and slightly thicker at the edges. For three beam paths this does not give significant error but allows a reduction of storage to one third of that otherwise required. This feature is further described below in relation to a different form of the apparatus.

In an alternative mode of operation of apparatus such as that of FIG. 1, the X-ray spot scan and collimators 18 can be arranged so that the fan effectively rotates about the body, with the region of irradiated detectors moving laterally in the opposite direction to the source spot. If the extent of anode 17 and detectors 19 is sufficient, the orbital motion may be dispensed with. In that case, the organization of the data can be similar to that described in U.S. Pat. Application Ser. No. 544,799, filedon Jan. 28, 1975. As a further alternative, the scanning X-ray source can be replaced by a conventional source such as a rotating anode tube, and the scan of the fan of X-rays relative to the detectors provided solely by orbital and/or lateral scanning motions of that source.

It should be noted that, in the arrangements described, afterglow in detector elements no longer being irradiated can still be intercepted by the photomultipliers and introduce some noise into the data. For this reason, scintillator crystals having low afterglow should be employed. The problem can be alleviated by the use of other detectors such as semiconductor diodes, which may be germanium photodiodes. Gas filled counters or other detectors may also be used. In those cases the grouping, if desired, may be by suitable multiplexing of the output signals. Alternatively, shutter means or similar may be provided to intercept the emitted light between the crystals and the associated photomultipliers.

Figure 3:
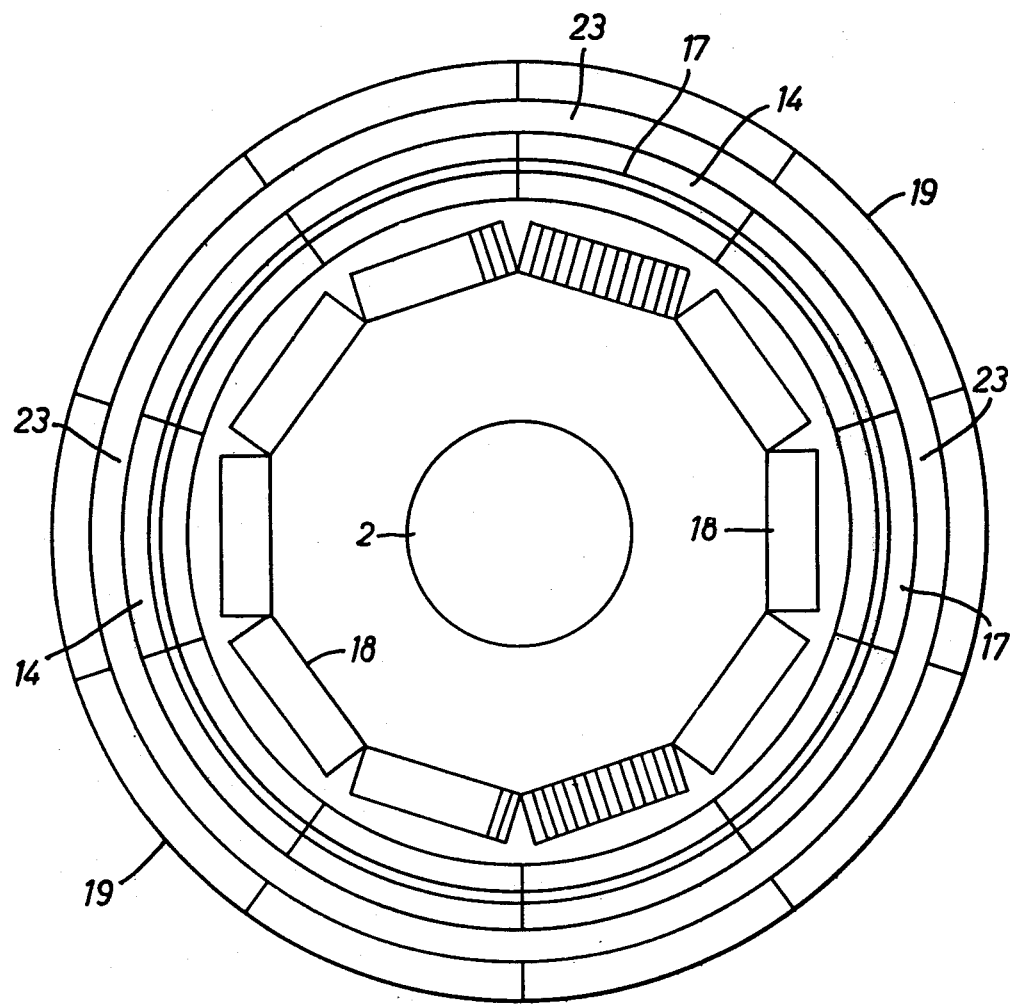
FIG. 3 shows an arrangement for an alternative embodiment of the invention.

FIG. 3 shows a development, of the arrangement described, for which the orbital movement, of X-ray source 14 and detector means 19, is not required. Aperture 2 is surrounded by a ring of individual scanning X-ray tubes 17 of which the glass envelopes, indicated at 23, are arranged to adjoin. Inside the ring of tubes 14, there is provided a ring of collimators 18. X-ray tubes 14, having anodes 17 and collimators 18, are essentially similar to those described in relation to FIG. 1, tubes 14 being fixed in relation to the body in aperture 2. Outside of tubes 14 there is provided a further ring comprising a plurality of detector means 19 each of which is as described hereinbefore.

At any time one of the tubes 14 is in operation, the X-rays being formed into a fan by collimators 18 nearest to the tube and thereafter passing through the body in aperture 2 to be received at a detector means 19 opposite. It will be understood that for this purpose, the ring of detector means 19 must be set in a sufficiently different plane from tubes 14 for the X-rays to reach the detectors unobstructed. This is a source of slight error in the desired data but such errors largely cancel for the data obtained from the 180° displaced detector. Collimators 18 may be arranged so that the beam passes through them after passing through the aperture 2 as well as before.

In operation, the X-ray tubes are operated in sequence so that the X-ray spot on the anode in effect orbits around the body in aperture 2. The ring of collimators 18 is arranged to rotate around aperture 2 but at a relatively slower rate than the rotation of the FIG. 1 arrangement. The angular velocity desired is such that the collimators move through an angle slightly less than the beam spread angle of the fan of X-rays 16 during one revolution of the X-ray spot. In the example shown in FIG. 3, the collimator is in ten sections so that, without rotation, the angle of the center beam of the fan would change by 36° when the spot moves from one section to the next. For the 1.8° fan of the example, the collimators rotate 1.8° in one spot revolution so that, when the spot returns to the same collimator section it begins to fill in the missing 36°. Thus, twenty revolutions of the spot are required to fill in all missing values. The exact number used is tailored to give a suitable degree of overlap between fan beams for adjacent positions to reduce noise of overlap between fan beams for adjacent positions to reduce noise problems. It will be apparent that this collimator movement changes the fan position by 0.18° as it crosses each section, but such a small error can be disregarded. It should be noted that any detectors not being irradiated may be switched out of the circuit by any suitable means to reduce noise problems further.

In an alternative mode of operation of the FIG. 3 arrangement, the fan of radiation may be of sufficient extent to encompass the entire region of interest in the body. In that case, in conjunction with larger source and detector sectors, the operation would be such that the position of the group of detectors irradiated by the fan in effect orbits about the body in the same direction as the source spot.

Figure 4:
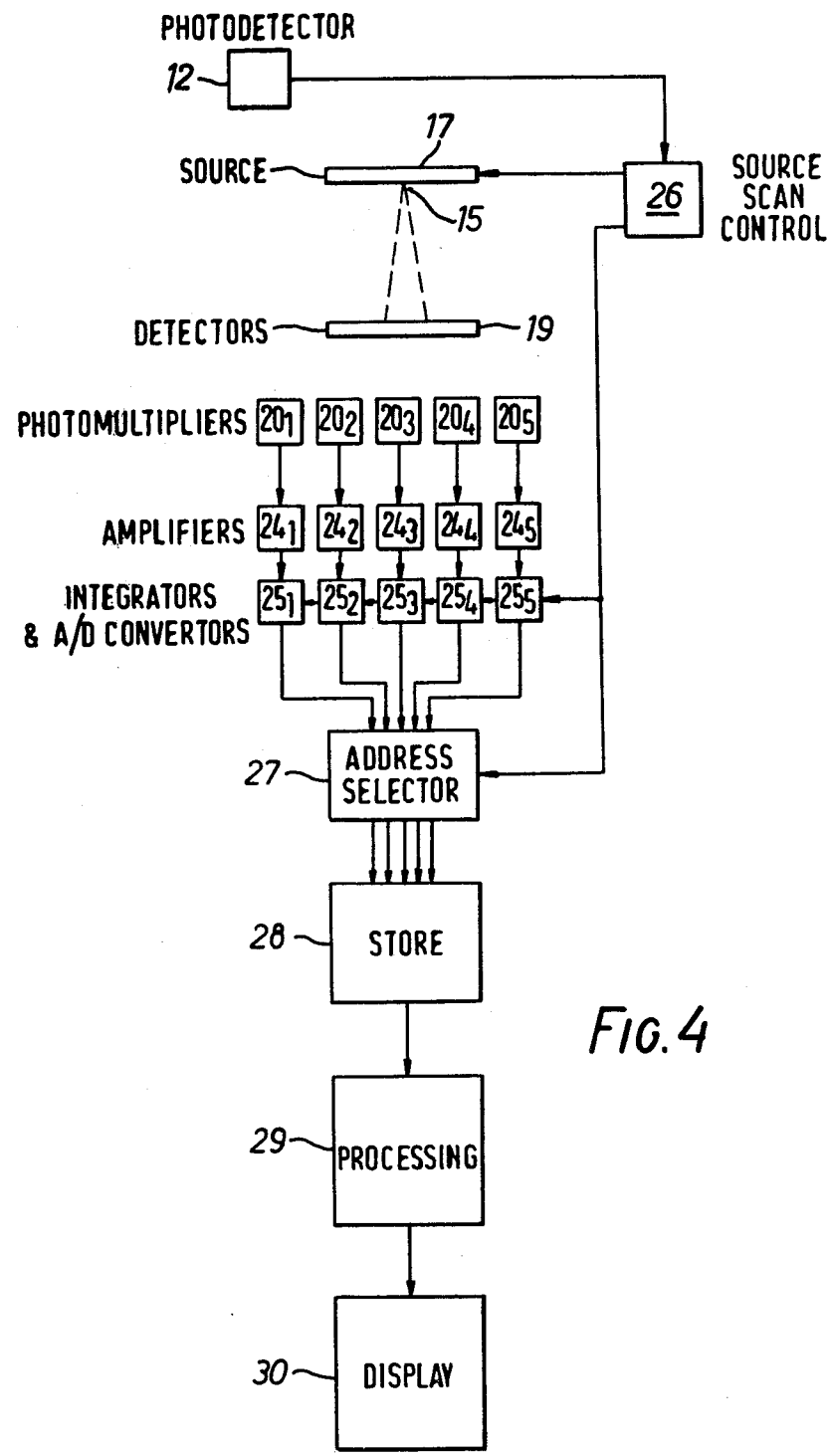
FIG. 4 shows in block diagrammatic form a circuit used for processing data derived from the apparatus.

FIG. 4 shows in simplified block diagrammatic form an arrangement for processing the output signals derived by the arrangement of FIG. 2, disregarding the steps required for combining adjacent detector outputs with appropriate delays. The five photomultipliers $20_1$ to $20_5$ are shown, although it will be understood that there may be a greater number of photomultipliers or outputs from a single photomultipler. The signals are amplified in amplifiers $24_1$ to $24_5$ and integrated and converted to digital form in converters $24_1$ to $25_5$. The integration period is as allowed by the progress of the scan of the X-ray source spot 15, and is controlled by signals from a scan control unit 26, which also controls the source spot 15. Scan control unit 26 also receives signals from photodetector unit 12, related to the progress of the orbital scan, so that the scan of source spot 15 can be properly related to the orbital movement. The data are provided to appropriate locations in a store 28 in response to an address selector 27. The locations in store 28 are chosen so that successive outputs from each photomultiplier are applied to storage locations representing beam paths at successive angles in the fan. After the fifth such angle, in this example, the data are applied to a new location representing a parallel beam path again at the first angle, and the cycle recommences. In this way, the data are allocated to storage locations representing five sets of data, each for parallel beam paths at one of the angles of beams in the fan, the allocation taking into account the grouping of outputs shown in FIG. 2. When store 28 contains data for the 5 complete sets of beam paths, properly sorted, this data is applied to a processing unit 29 for processing, for example, as described in U.S. Pat. No. 3,924,129 or in U.S. Pat. No. 3,778,614. The processing derives absorption values for individual elements of a matrix of elements notionally delineated in the planar (or substantially planar) slice being examined. The values are then provided as signals applied to correponding elements of a representation on a display unit 30. Unit 30 may be a cathode ray tube, line printer or other suitable output device. Alternatively, it may be applied to permanent storage, not shown, for future display.

The apparatus described hereinbefore is intended to acquire all the required data in a very short time, possibly as short as one hundredth of a second for the arrangement of FIG. 3. A suitable analogue to digital converter should be employed to meet such rates of acquisition. Such a converter may operate in the known manner of converting the output of a digital counter to analogue form and counting up or down to match that output to the input voltage. However, it may be divided into a plurality of sections each to convert to digital form signals between preset threshold levels, to operate at a faster rate.

The arrangement mentioned hereinbefore, for combining the outputs of different detectors with appropriate delays, is now described in greater detail. It has been mentioned that this arrangement may be used in conjunction with several different forms of the apparatus. The following description will therefore assume a form of the apparatus essentially the same as that described in greater detail in U.S. Pat. No. 3,946,234, in which a fan shaped spread or swath of X-rays is laterally scanned by means of mechanical scanning and in which a fixed bank of individual detectors is also mechanically laterally scanned so that each beam, at a particular orientation in the fan, is examined by a single detector at all times.

Figure 5:
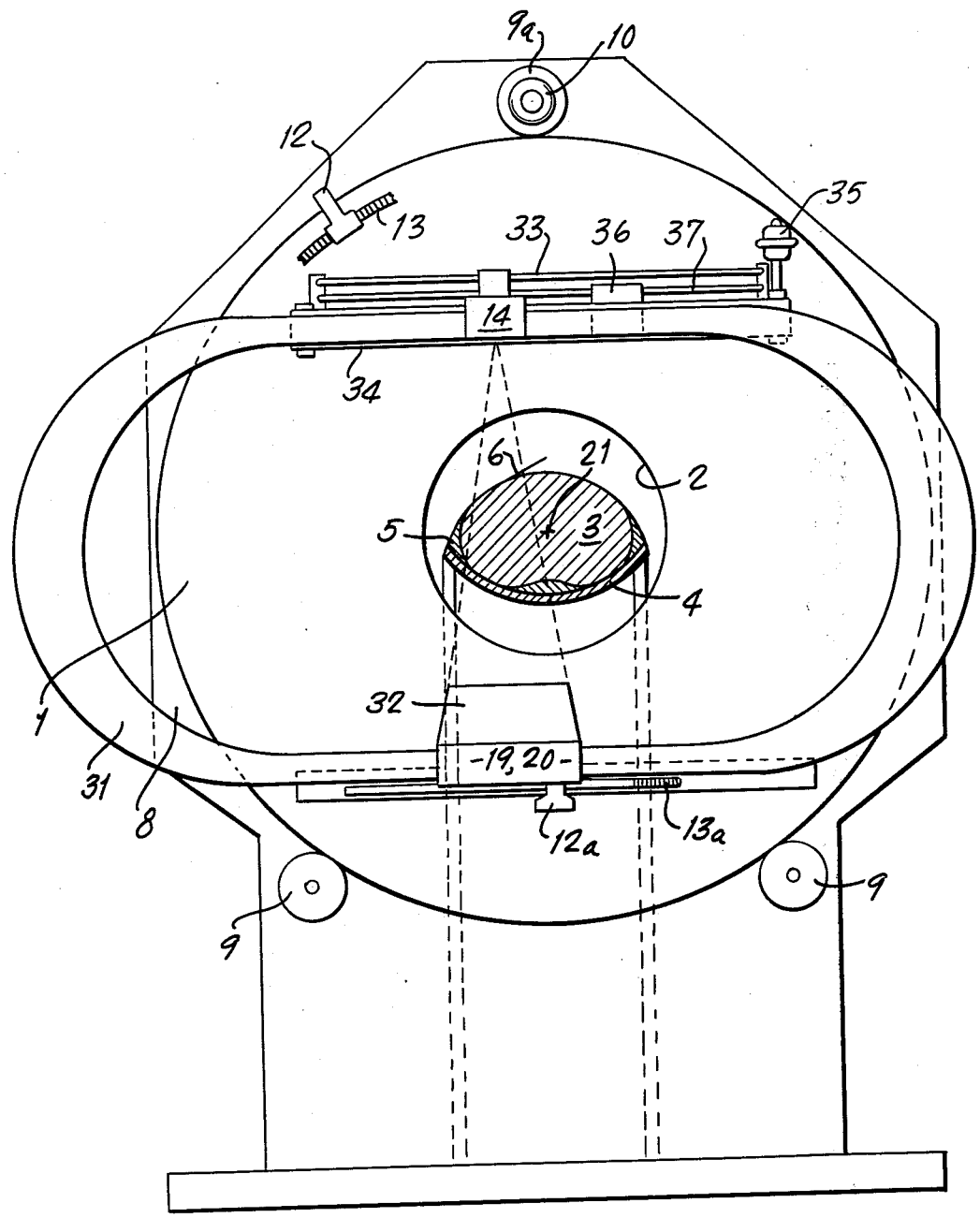
FIG. 5 shows in simplified form another form of an apparatus incorporating the invention.

A simplified form of this apparatus is shown in FIG. 5, similar elements being indicated by the same reference numerals as in FIG. 1. The source 14, which in this example does not include electronic scanning, is rigidly linked to the detector unit 19, 20, in this example individual scintillator crystals with associated individual photomultipliers, by a yoke 31. Detector unit 19, 20 has as associated collimator unit 32 comprising individual collimators helping to define the X-ray beam incident on each detector and to exclude scattered radiation therefrom. To provide lateral scanning of source 14 and, via yoke 31, the detectors, the source is mounted on a track 33 and driven via a belt 34 by a reversible motor 35. A counterweight 36 running on a track 37 is provided on the opposite run of belt 34 to counter out-of-balance forces due to the mass of source 14.

An additional graticule 13a and photocell unit 12a are provided to monitor the lateral scanning motion.

In operation, the motor 10 causes a stepped orbital motion, and between each step motor 35 causes a scan of source 14 and detectors 19, 20 either to right or left. During this scan, the integrators 25, not shown in this Figure, cause output readings to relate to discrete beam paths, each detector providing readings for a set of parallel beam paths at a slightly different orientation. These readings are repeated for different angular positions in the rotational motion. Of course, if desired, provision can be made for a continuous orbital motion.

Figure 6A:
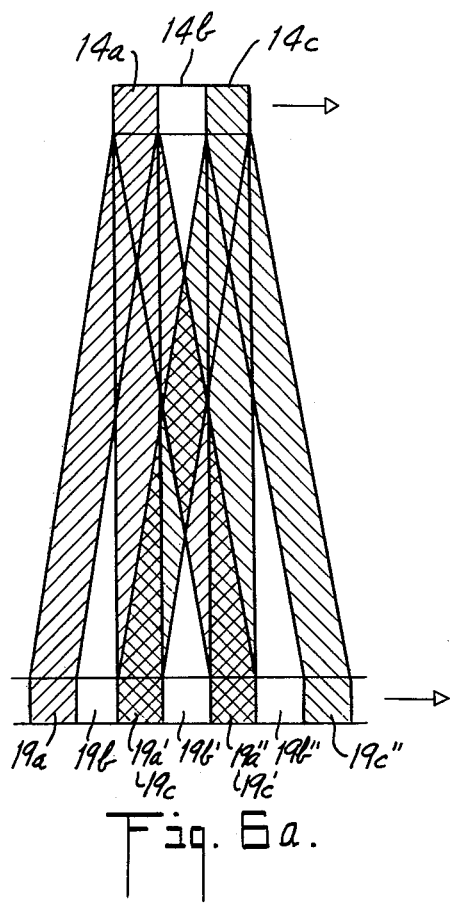
FIG. 6 illustrates the combination of beam paths for the invention.

FIG. 6a illustrates the beam paths irradiated in the course of part of a lateral scan by beams incident on a group of three adjacent ones of the detectors included in 19, 20. It is emphasised that the Figure is a simplified diagram intended to illustrate the principle of the invention and does not show an actual distribution of beam paths. The differences from the real situation are at least that (1) the beam paths for one detector are shown adjacent, although in practice they overlap, (2) the beam paths are shown of exaggerated width and (3) they are shown at exaggerated angular spacing.

In FIG. 6a the source at position 14a provides three beams, shown cross hatched, incident on three detectors 19a, 19a' and 19a". At position 14b the beams, not cross hatched, are incident on the detectors at 19b, 19b' and 19b", and at 14c the beams, cross hatched at an opposite inclination, are incident on the detectors at 19c, 19c' and 19c" (where 19a' and 19c designate the same detector, and so do 19a" and 19c'). The arrangement of data processing is then such that data for the right hand beam of 14a is stored for a time $\tau$ until the data for the middle beam of 14b is available, and is then added thereto. The two are then stored for a further time $\tau$ until the data for the left hand beam of 14c is available, and are then added to that also. The total forms a data signal for a composite beam which is shown in said outline in FIG. 6b.

Figure 6B:
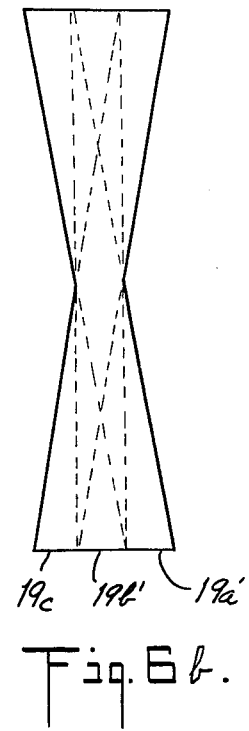
Figure 7:
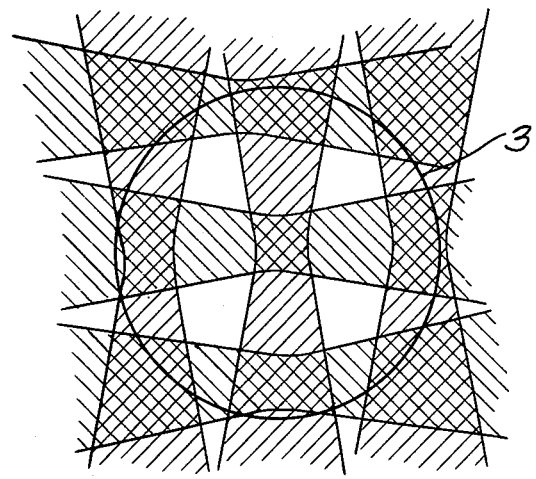
FIG. 7 shows the distribution of some of these beam paths through a body.

Considering the form of composite beam shown in FIG. 6b, it can be seen that the beam is narrower in the center, being substantially the same width as a single beam, than at the outside. Of course, the actual shape obtained depends on the scanning motions used and the actual beams combined, but the narrow center is a characteristic feature of all such beams. In the course of the complete scan, the body 3 is irradiated by a large number of beams such as that of FIG. 6b, from many directions. A few of these are shown in the simplified diagram of FIG. 7. It will be apparent that the center of the body is examined only by the narrowest parts of the beams, while the outer regions are examined by both narrow and wide parts. It should be noted that in FIG. 7 the relative scales of the composite beams to the body 3 have been exaggerated for the purposes of explanation. Since the resolution of examination is, as will be apparent, inversely dependent on the width of the beams being used, it will be seen that greater resolution is obtained at the center than at the edges of the body. Despite this, the processing requires no greater storage than if the same number of wider beams were used, as would otherwise be required to adequately cover the outer regions. Normally, greater resolution is required at the center of the picture than at the edges. However, if this is not the case, the bed 4 can be arranged to be moveable to place a required part of the body 3 into the high resolution region at the scan center.

Figure 8:
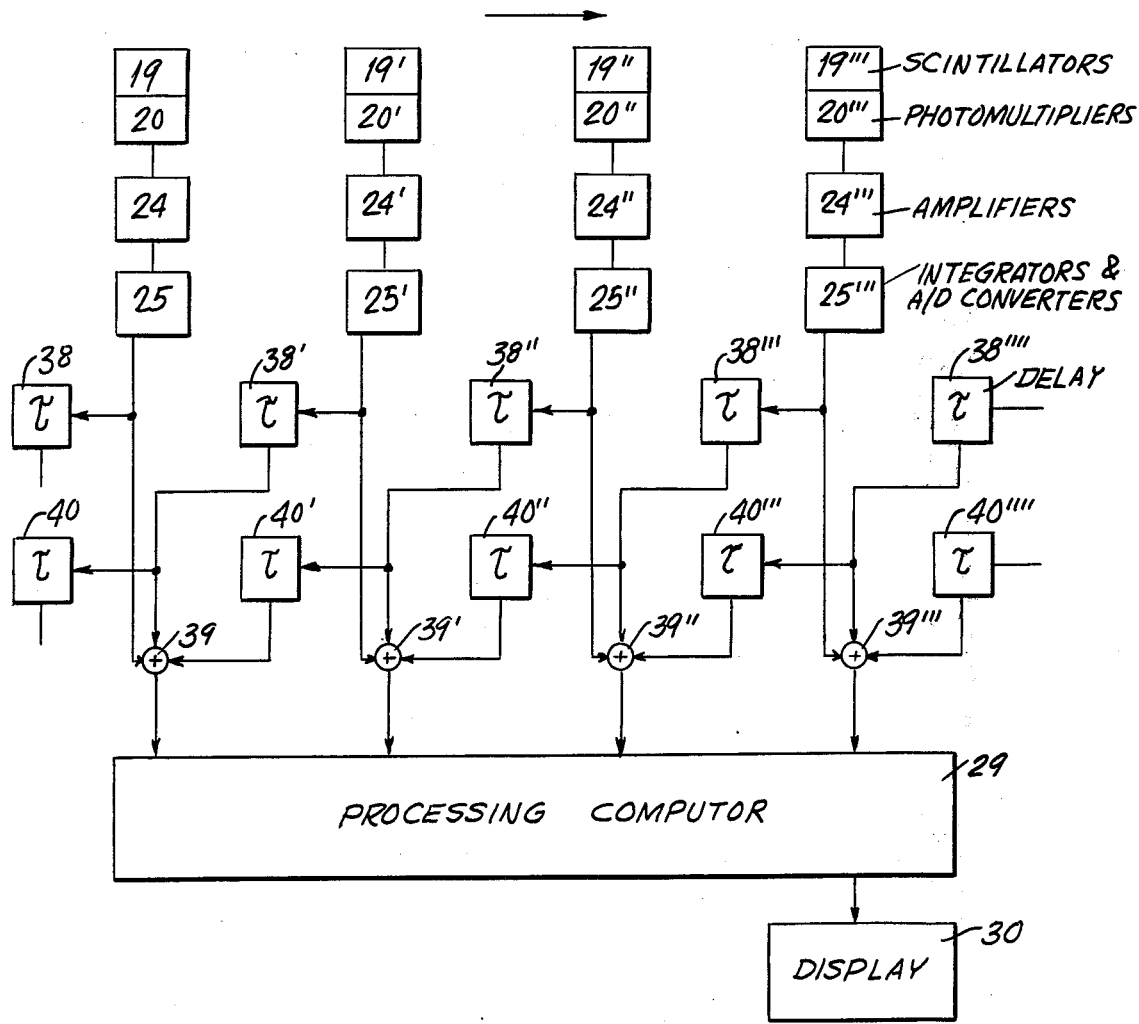
FIG. 8 shows an exemplary circuit for organizing the data in accordance with the principles of the invention.

There is shown, in FIG. 8, a block diagrammatic circuit for combining the data appropriately. Considering FIG. 6b, it will be seen that the composite beam is formed from the first data (a) from detector 19", (delayed by $2\tau$), the second data (b) from detector 19' (delayed by $\tau$) and the third data (c) from detector 19 (undelayed). In the arrangement of FIG. 8, each individual scintillator 19 and photomultiplier 20 feed respective amplifiers 24 and integrators and A/D converters 25. Each signal is applied to a first delay of ($\tau$) 38 and an adder 39. The output from the delay 38 for the following detector is also fed to added 39 and to a second delay of (τ) 40. The output of the following delay 40 is also fed to the adder 39. All outputs of adders 39 are applied to the processing computer 29, and the results of processing are displayed on display unit 30. Logarithmic converters can be included in the processing where appropriate as outlined in the patents referred to hereinbefore.

The input 41 to processing computer 29 (which may be of the type disclosed in U.S. Pat. No. 3,778,614 or U.S. Pat. No. 3,924,129) may be considered as typical. It will be seen that an input at one time comprises the sum of the direct output of detector 19, the output of detector 19' delayed by τ and the output of detector 19" delayed by 2τ, which is the group of output signals required for the composite beam of FIG. 6b. If desired, the required composite output signal may be provided by placing all the data at individual locations of a store and withdrawing them as appropriate for combination. A similar effect may be obtained by deriving three sets of data for the undelayed, once delayed and twice delayed beams, and combining these during or after processing.

It will be appreciated that the invention is not limited to the forms described hereinbefore and that other arrangements may be devised.

I claim:

1. An apparatus for examining a body by means of penetrating radiation including means for generating output signals, representative of the absorption suffered by the radiation in passage along respective beam paths through a region of the body, for processing to provide a representation of the distribution of absorption of the radiation in the region, and combining means for combining groups of output signals relating to groups of beam paths, chosen so that the beam paths of a group are inclined to one another and pass through a common elemental area of the region, to provide composite output signals representing the absorption of the radiation in passage through the body along composite beam paths which are narrower in the vicinity of the respective elemental areas than in other parts of the region, so that said processing can be effected on a plurality of output signals including at least some of said composite output signals.

2. An apparatus according to claim 1 wherein the means for generating output signals comprise source means arranged to irradiate a region of the body, detector means arranged to provide said output signals and scanning means adapted to scan the radiation in relation to the body so as to irradiate said region along a plurality of beam paths passing through the body from a plurality of directions.

3. An apparatus according to claim 2 wherein said scanning means comprises means for scanning the source means and the detector means laterally in a plane intersecting the body and means for orbiting the source means and detector means about a common axis which intersects said plane.

4. An apparatus according to claim 2 wherein the source means is arranged to irradiate the region along a swath of said radiation and the detector means comprises a plurality of detector devices arranged to provide output signals representative of the absorption suffered by the radiation along different paths within the swath.

5. An apparatus according to claim 4 wherein the scanning means includes means for orbiting the source means about the body so as to direct said swath at the body from a plurality of directions.

6. An apparatus according to claim 5 wherein the scanning means further includes means for laterally traversing the source means in relation to the body.

7. An apparatus according to claim 2 wherein the combining means includes means for delaying an output signal relating to a beam path passing through an elemental area and means for adding the delayed output signal to another output signal, relating to another beam path passing through the area, provided by the detector means at a later time.

8. An apparatus according to claim 2 wherein said scanning means and combining means are arranged so that said elemental areas are in a predetermined part of said region so that a representation derived by processing the output signal is of greater resolution in said predetermined part than in other parts of the region.

9. An apparatus according to claim 1 including processing means for processing output signals including at least some of said composite signals to evaluate an absorption or transmission coefficient, with respect to said radiation, at each of a plurality of loations in said region.

10. An apparatus according to claim 9 including display means for displaying a representation of the distribution of said coefficients in at least part of said region.

11. An apparatus, for examining a body by means of penetrating radiation, including a source of radiation directed through a region of the body, detector means arranged to provide output signals indicative of the intensity of the radiation after passage through said region, scanning means adapted to scan the source about the body so as to direct the radiation therethrough from a plurality of different directions, and combining means arranged to combine groups of output signals, relating to beam path of which some at least are inclined to one another, to provide composite output signals, each representing the intensity of radiation transmitted through the body along a composite beam path which is narrower in the vicinity of a respective elemental area of said region than in other parts of said body and at its beginning and end portion, for processing to provide a representation of the distribution of absorption of the radiation in the region.

12. An apparatus according to claim 11 including processing means for evaluating, from at least some of said output signal and composite output signals, an absorption or transmission coefficient, with respect to said radiation, for each of a plurality of locations in said region.

13. An apparatus according to claim 12 including display means for displaying a representation of the distribution of said coefficients in at least part of said region.

14. Medical radiology apparatus including:
means defining a patient position and means disposed outside the patient position for generating penetrating radiation intersecting a region including the patient position and emerging therefrom after suffering absorption determined by matter through which it has travelled;
means for detecting the radiation emergent from the region to provide output signals each indicative of the intensity of radiation received thereby after passage through the region along a respective one of a plurality of beam paths at different orientations in the patient position;

means for combining groups of the output signals so as to provide composite output signals relating to beam paths which are inclined to one another and intersect within the region each indicative of the intensity of radiation received at the detector means after passage through the region along a composite beam path which is wider at its points of entrance to and exit from the region than at a point therebetween; and means for processing output signals, at least some of which are composite output signals to construct a representation of the distribution of absorption of the radiation within at least part of the region.

* * * * *